United States Patent [19]

Likins, Jr. et al.

[11] 4,351,818
[45] Sep. 28, 1982

[54] CARBON BLACK FURNACE PROCESS

[75] Inventors: Merle R. Likins, Jr.; Galen D. Stacy, both of Bartlesville, Okla.

[73] Assignee: Phillips Petroleum Company, Bartlesville, Okla.

[21] Appl. No.: 211,984

[22] Filed: Dec. 1, 1980

[51] Int. Cl.$^3$ .......................... C01B 31/02; C09C 1/48
[52] U.S. Cl. .................................. 423/450; 423/449; 23/230 A; 422/62
[58] Field of Search .............. 423/449, 450; 23/230 A; 422/150, 62

[56] References Cited

U.S. PATENT DOCUMENTS

| | | | |
|---|---|---|---|
| 2,844,443 | 7/1958 | King | 23/209.6 |
| 3,005,688 | 10/1961 | Williams | 23/259.5 |
| 3,095,273 | 6/1963 | Austin | 23/209.6 |
| 3,169,047 | 2/1965 | Osburn, Jr. | 23/209.4 |
| 3,350,173 | 10/1967 | Colby et al. | 23/209.4 |
| 3,369,870 | 2/1968 | Ganz et al. | 23/209.4 |
| 3,390,960 | 7/1968 | Forseth | 23/209.4 |
| 3,401,020 | 9/1968 | Kester et al. | 23/209.4 |
| 3,471,260 | 10/1969 | Lehr et al. | 23/209.4 |
| 3,592,599 | 7/1971 | Gohlke et al. | 23/209.4 |
| 3,637,350 | 1/1972 | Thomas | 23/209.4 |
| 3,993,447 | 11/1976 | Buss et al. | 23/259.5 |
| 4,080,434 | 3/1978 | Buss | 423/450 |
| 4,144,997 | 3/1979 | Anderson et al. | 236/15 BF |

Primary Examiner—O. R. Vertiz
Assistant Examiner—Gregory A. Heller

[57] ABSTRACT

The flow rate of quench fluid in a furnace process is manipulated in response to the water content of process air.

8 Claims, 1 Drawing Figure

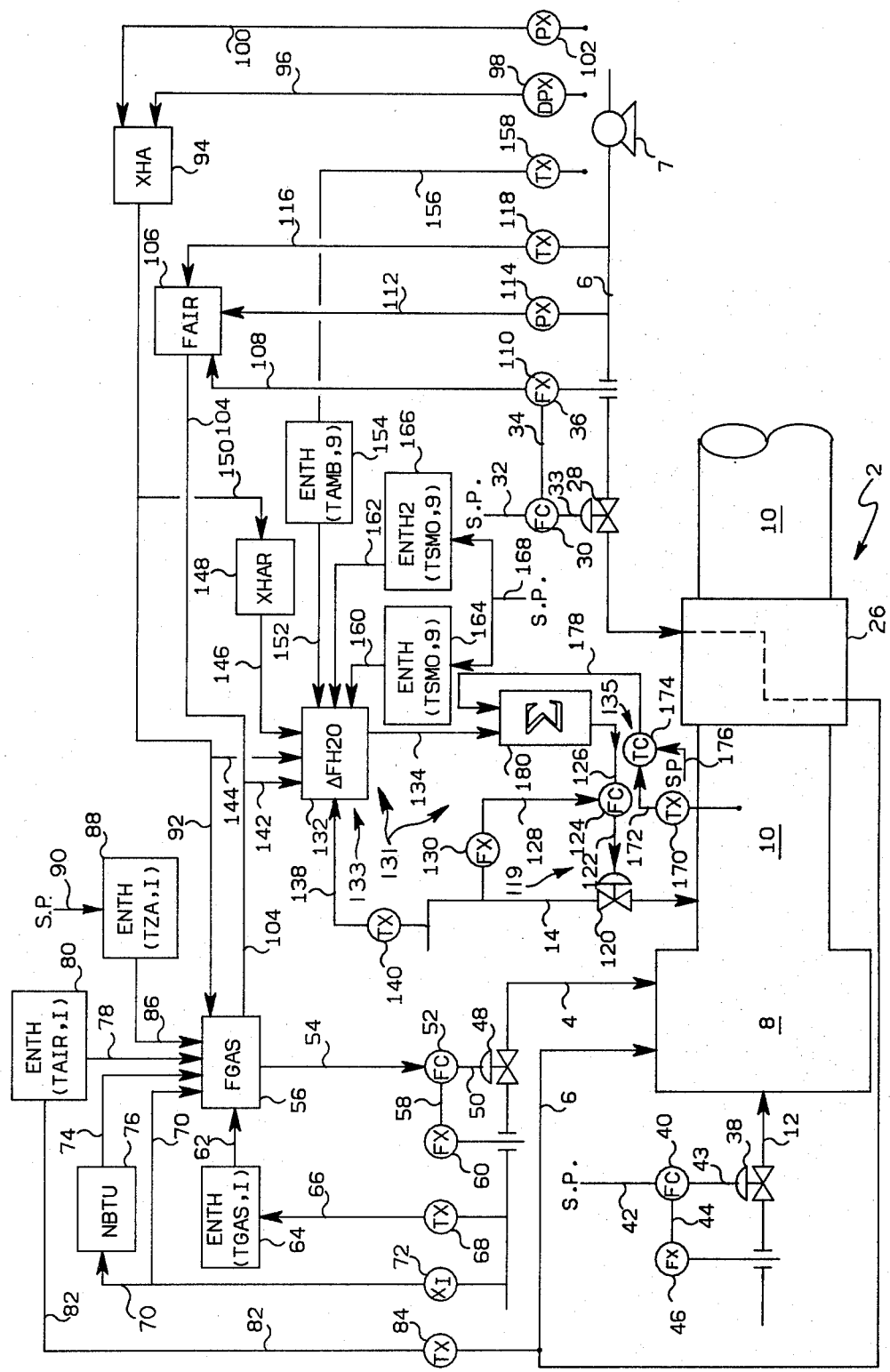

CARBON BLACK FURNACE PROCESS

BACKGROUND

The invention relates to process control. In another aspect, the invention relates to a furnace. In a further aspect, the invention relates to an energy efficient carbon black reactor and its use.

In certain types of furnaces, temperature control is extremely important, as excessive temperatures can damage the furnace. Where the furnace is employed to carry out a process, such as the production of carbon black, the temperature within the furnace is desirably maintained within a relatively narrow range, so as to produce attractive quantities of a desirable product.

A problem which has long existed in the art is that of accurately measuring the temperature within the furnace for control purposes. Conventional temperature sensors cannot long withstand the extremely elevated temperatures encountered in a furnace, typically in excess of 2000° F. Reliable temperature control in a furnace, especially where the characteristics of the air and fuel which are combusted in the furnace are subject to fluctuation, has proved a difficult problem. Fuel characteristics which can vary from time to time include its temperature and composition. Air characteristics which can vary significantly from time to time include its temperature, pressure, and relative humidity.

Especially in processes for the production of carbon black, waste heat which was not utilized in the pyrolysis reaction escapes the furnace in the gaseous effluent. It would be extremely desirable to capture and recycle as much of this waste heat as possible thereby reducing the amount of fuel required to maintain the desired furnace temperature. Due to the high temperatures involved, it would be further desirable to control recycle of heat without undertaking a direct measurement of maximum furnace temperature.

OBJECTS OF THE INVENTION

It is an object of this invention to provide an apparatus for recycling waste heat back into a furnace, thereby conserving fuel.

It is another object of this invention to provide a process for recycling waste heat back into a furnace, thereby conserving fuel.

SUMMARY OF THE INVENTION

According to one embodiment of the invention, a furnace employing indirect heat transfer between its outgoing effluent and incoming combustion supporting air and a quench of its outgoing effluent prior to indirect heat exchange with the incoming air is provided with a means for regulating its flow of quench at least partially in response to the water content of the incoming air. In a prior art apparatus employing a means for regulating the flow of quench in response to the temperature of the quenched effluent, it was found, surprisingly, that furnace temperature frequently declined as ambient temperature increased. This anomaly was traced to the containment in the air stream of greater amounts of water vapor at higher temperatures. To compensate for the fall in furnace temperature, the fuel rate in the prior art apparatus was increased. By utilizing the apparatus of the present invention, the drop in furnace temperature caused by a rising dew point can be anticipated, and the rate of quench flow reduced before furnace temperature drops significantly. The combustion supporting air is thus preheated to a higher temperature in times of rising humidity than in the prior art apparatus, and waste heat is more efficiently utilized to maintain furnace temperature than in the prior art apparatus, which utilized a greater flow of fuel in times of rising humidity to maintain desired furnace temperature.

According to another embodiment of the invention, the rate of quench fluid flow to a furnace is controlled in response to a signal which is derived at least in part from the relative humidity of the air supplied to the furnace.

BRIEF DESCRIPTION OF THE DRAWINGS

The FIGURE is a schematic illustrating certain features of the present invention.

DETAILED DESCRIPTION OF THE INVENTION

Referring to the FIGURE, a furnace 2 is provided with a conduit 4 for the introduction of combustible material and a conduit 6 for the introduction of combustion-supporting gas. Preferably, the conduit 4 communicates with a gaseous hydrocarbon fuel supply, such as natural gas, and the conduit 6 communicates with a source of free oxygen-containing gas, such as air. Preferably, air is caused to flow through the conduit 6 by a blower 7 associated therewith. The fuel from conduit 4 and air from conduit 6 are admixed and combusted in the furnace 2 to form a heated mass of combustion gases which flows as a stream from a zone 8 of the furnace 2 and through an effluent conduit 10.

In a preferred embodiment, the furnace 2 is a carbon black reactor. A conduit 12 for the introduction of a carbonaceous feedstock communicates with the zone 8. Feed introduced into the furnace via the conduit 12 contacts the hot combustion gases and decomposes to form carbon black. In this case, the effluent conduit 10 carries particulate carbon black suspended in the combustion gases.

It is desirable during the manufacture of carbon black that the fuel introduced into the furnace 2 via the line 4 be essentially completely combusted prior to the point in the combustion gas stream where the carbonaceous feedstock is introduced by the line 12. This is commonly achieved by combusting the fuel and air in combustion tunnels (not shown) oriented tangentially to the zone 8, as is well known by those skilled in the art, (see, for example, U.S. Pat. No. 2,564,700) although the present invention is not limited to carbon black reactors employing tangential combustion tunnels.

It is also desirable to cool the effluent stream in conduit 10 to a manageable temperature during the production of carbon black. To this end, a quench fluid, for example, water or cool gases are introduced into the conduit 10 via a conduit 14 which communicates with the conduit 10 to cool the effluent stream. The effluent in the conduit 10 is cooled from a temperature of 2400° or more to a temperature of 2000° F. or less, generally to a quenched effluent temperature of between about 800° F. and about 1800° F., to avoid heat induced damage to the materials from which the conduit 10 is formed, for example, cast refractory, or damage to other downstream equipment.

According to one aspect of the present invention, the air in line 6 is preheated before introduction into the furnace 2 by indirect contact in heat exchange relationship with the effluent flowing through the conduit 10.

Preferably, the air is preheated in a heat exchanger 26 which is associated with the conduit 10 downstream of introduction of quench fluid from the conduit 14. Usually, because of ease of fabrication and low maintenance requirements, the heat exchanger 26 comprises a jacket in communication with the line 6 and surrounding a portion of the exterior of the conduit 10. Thus, at least a portion of the air line 6 is in heat exchange relationship with a portion of the effluent conduit 10. A suitable spiral partition can be positioned in the jacket, if desired, to cause a spiral flow of the air around the exterior of the conduit 10 and in countercurrent relationship with the flow of effluent through the conduit 10, to cause good indirect heat transfer between the incoming air and the outgoing effluent. See, for example, U.S. Pat. No. 3,369,870. Other types of heat exchangers can be employed if desired, but generally at some sacrifice in pressure drop through the conduit 10.

A valve 28 positioned in the line 6 allows control of the rate of air flow through the conduit 6. Preferably, a motor valve is deployed in the line 6 upstream of the heat exchanger 26 to effect flow control. A flow controller 30 is operably associated with the motor valve 28 and compares a set point signal 32 representative of the desired flow through the conduit 6 with a signal 34 which is representative of the actual flow through the conduit 6. The valve 28 is manipulated in response to a signal 33 from the flow controller 30 which is established in response to the comparison of the actual and desired flow signals, for example, so as to decrease the difference between the signals 32 and 34. The signal 34 is established by a means 36 associated with the conduit 6 for establishing a signal representative of the flow of air through the conduit 6, such as a flow transducer. In this manner, the air flow rate through the conduit 6 can be adequately controlled.

In similar fashion, the flow rate of carbonaceous feedstock, when employed, is controlled by a valve 38, such as a motor valve, disposed within the line 12. The valve 38 is manipulated by a flow controller 40 which compares a set point signal 42 representative of a desired flow rate of carbonaceous feedstock with a signal 44 representative of the rate of flow in the conduit 12. The signal 44 is established by a flow transducer 46 associated with the conduit 12. The flow controller 40 establishes a signal 43 and the valve 40 is manipulated in response to the signal 43 to control the rate of flow in the conduit 12, such as by being manipulated so as to decrease the difference between the signals 42 and 44.

In accordance with another aspect of the present invention, the rate of fuel flow in the conduit 4 is controlled by a valve 48 disposed within the conduit 4. The valve 48 is manipulated in response to a signal 50 from a flow controller 52. The signal 50 can be mechanical, electrical, hydraulic or pneumatic in nature, for example. The flow controller 52 receives a set point signal 54 representative of a desired flow rate in the conduit 4, preferably from a computer 56, and a flow rate signal 58 which is representative of the flow rate of fuel in the conduit 4, from a means 60 associated with the conduit 4 for establishing a signal representative of the flow rate of fuel in the conduit 4, such as a flow transducer. The signal 50 is established by the flow controller 52 in response to the signals 54 and 58. The valve 48 is manipulated in response to the signal 50 to control the rate of flow through the conduit 4, such as by being manipulated so as to decrease the difference between the signals 54 and 58.

The fuel rate set point signal 54 (FGAS) is preferably established by the computer 56 in response to a relationship between:

(a) the enthalpies of the components (I) of the fuel gas stream 4 at the fuel gas temperature (TGAS);

(b) the relative composition of the fuel gas stream, such as the mole percent (X) of each component (I) in the fuel gas stream 4;

(c) the heat of combustion (NBTU) of the fuel gas stream 4 per standard unit of volume;

(d) the enthalpies of the components (I) of the preheated air stream 6 at the preheated air stream temperature (TAIR);

(e) the enthalpies of the components (I) of the combustion gas stream 10 at the desired combustion gas temperature (TZA);

(f) the moisture content of air entering the conduit 6, such as the mole fraction of water vapor (XHA) in the preheated air stream 6 expressed as the ratio moles water vapor/moles dry air; and (g) the standardized total flow rate (FAIR) of air flowing through the conduit 6.

For example, a preferred relationship for establishing the signal 54 in units of thousands of standard cubic feet per hour from the above parameters can be expressed as:

$$\begin{aligned}
FGAS = \ & FAIR*[XHA*ENTH(TZA,9) + (0.79+X_{N2}) \\
& *ENTH(TZA,14) + 0.21*ENTH(TZA,13)- \\
& ENTH(TAIR,8) - XHA*ENTH(TAIR,9)]/ \\
& [379*NBTU + X_{N2}*ENTH(TGAS,1) + X_{CH4} \\
& *ENTH(TGAS,3) + X_{C2}*ENTH(TGAS,4) \\
& + X_{C3}*ENTH(TGAS,5) + X_{C4}*ENTH(TGAS,6) \\
& + (X_H + X_{C6} + X_{C5})*ENTH(TGAS,7) - \\
& (7*X_H+6*X_{C6}+5*X_{C5}+4*X_{C4}+3*X_{C3} \\
& +2*X_{C2}+X_{CH4})*ENTH(TZA,10) - \\
& (8*X_H+7*X_6+6*X_{C5}+5*X_{C4} + \\
& 4*X_{C3}+3*X_{C2}+2*X_{CH4})*ENTH \\
& (TZA,9)+(11*X_H + 9.5*X_{C6}+8*X_{C5} \\
& +6.5*X_{C4}+5*X_{C3}+3.5*X_{C2}+2 \\
& *X_{CH4})*ENTH(TZA,13)].
\end{aligned}$$

This and other relationships set forth in this specification are preferably solved by a digital computer adapted to periodically solve the relationship from sensed inputs, such as once about every 6 seconds.

In the above equation, the term ENTH(T,I) is representative of the enthalpy of component I at temperature T. The (T,I) terms utilized in this specification are defined as follows:

TABLE I

Fuel Temp, T = TGAS
Preheated Air Temp, T = TAIR
Ambient Air Temp, T = TAMB
Desired Flame Temp, T = TZA
Desired Quenched Smoke Temp, T = TSMO
Quench Water Temp, T = TH2O
$N_2$, I = 1
$CO_2$, I = 2
$CH_4$, I = 3
$C_2$, I = 4

TABLE I-continued

C$_3$, I = 5
C$_4$, I = 6
C$_5$, I = 7
Air, I = 8
H$_2$O, I = 9
CO$_2$, I = 10
CO, I = 11
H$_2$H$_2$, I = 12
O$_2$, I = 13
N$_2$, I = 14
CH$_4$, I = 15
H$_2$, I = 16
Oil, I = 17

The term $X_I$ in the FGAS equation is representative of the mole percent X of component I in the fuel stream 4, where I is defined as follows:

TABLE II

| Component | I |
|---|---|
| methane | CH$_4$ |
| acetylene, ethylene, ethane | C$_2$ |
| propyne, propene, propane | C$_3$ |
| butyne, butenes, butane | C$_4$ |
| pentyne, pentenes, pentane | C$_5$ |
| hexyne, hexenes, benzene, hexane | C$_6$ |
| heavies | C$_H$ |

At least one signal 62 representative of ENTH(TGAS,1), ENTH(TGAS,3), ENTH(TGAS,4), ENTH(TGAS,5), ENTH(TGAS,6) and ENTH(TGAS,7) is established by a means 64 for establishing signals representative of the enthalpies of the components in the fuel gas stream 4. The at least one signal 62 is received by the computer 56. Preferably, the means 64 is a computer or subassembly capable of solving the relationships $$\text{ENTH(TGAS,1)} = (6.94)(\text{TGAS}) + (0.00010115)(\text{TGAS})^2 - 416.76$$

$$\text{ENTH(TGAS,3)} = (8.25)(\text{TGAS}) + (0.0024166)(\text{TGAS})^2 - 504$$

$$\text{ENTH(TGAS,4)} = (11.699)(\text{TGAS}) + (0.0068702)(\text{TGAS})^2 - 726.68$$

$$\text{ENTH(TGAS,5)} = (16.865)(\text{TGAS}) - (0.0062446)(\text{TGAS})^2 + (0.000093069)(\text{TGAS})^3 - 1009.6$$

$$\text{ENTH(TGAS,8)} = (21.01)(\text{TGAS}) + (0.15488)(\text{TGAS})^2 - 1316.3$$

$$\text{ENTH(TGAS,7)} = (26.077)(\text{TGAS}) + (0.01934)(\text{TGAS})^2 - 1634$$

where enthalpy is in BTU/mole and TGAS is in °F. The at least one signal 62 is established by the means 64 in response to a signal 66 established by a means 68 associated with the conduit 4 for establishing a signal representative of the temperature of the fuel gas stream, such as a temperature transducer. The signal 66 is received by the means 64.

At least one signal 70 representative of $X_{N2}$, $X_{CH4}$, $X_{C2}$, $X_{C3}$, $X_{C4}$, $X_{C5}$, $X_{C6}$ and $X_H$ is established by a means 72 associated with the conduit 4 for establishing signals representative of the relative composition of the fuel gas stream 4. The at least one signal 70 is received by the computer 56. A suitable means 72 is a chromatographic analyzer.

A signal 74 representative of the net heating value per unit volume, NBTU, of the fuel gas stream 4 is established by a suitable means 76 for establishing a signal representative of the heating value of the fuel gas flowing in conduit 4. The signal 74 is received by the computer 56. The heating value of the fuel gas can be expressed in terms of energy units per standard unit of volume, BTU per standard cubic foot, for example, which the fuel gas will produce when completely combusted. The means 76 receives at least signal 70 for deriving the value of the fuel gas stream from the chromatographic analyzer 72 and establishes the signal 74 in response thereto. One technique for deriving such a value from a chromatographic analysis is disclosed by R. L. Kindred et al. in U.S. Pat. No. 3,095,728.

At least one signal 78 representative of ENTH(TAIR, 8) and ENTH(TAIR,9) is established by a suitable means 80 for establishing signals representative of the enthalpies of the components in the preheated air stream 6. The at least one signal 78 is received by the computer 56. Preferably, the means 80 comprises a computer or subassembly capable of solving the relationships:

$$\text{ENTH(TAIR,8)} = (6.9065)(\text{TAIR}) + (0.000082564)(\text{TAIR})^2 + (0.00000018764)(\text{TAIR})^3 - 414.73$$

$$\text{ENTH(TAIR,9)} = (7.93163)(\text{TAIR}) + (0.000711015)(\text{TAIR})^2 - 414.95$$

where enthalpy is in BTU/mole and TAIR is in °F. For solution of the above relationships, the means 80 receives a signal 82 representative of the temperature of the preheated air in the conduit 6 and establishes the at least one signal 78 in response thereto. The signal 82 is established by a means 84 associated with the conduit 6 for establishing a signal representative of the temperature of the preheated air in the conduit 6, such as a temperature transducer.

At least one signal 86 representative of ENTH(TZA,9), ENTH(TZA,14), ENTH(TZA,13) and ENTH(TZA,10) is established by a suitable means 88 for establishing signals representative of the enthalpies of the components in the combustion gases formed in the zone 8. The at least one signal 86 is received by the computer 56. Preferably, the means 88 comprises a computer or subassembly capable of solving the relationships $$\text{ENTH(TZA,9)} = (7.93163)(\text{TZA}) + (0.000711015)(\text{TZA})^2 - 414.95$$

$$\text{ENTH(TZA,10)} = (11.0865)(\text{TZA}) + (0.00063853)(\text{TZA})^2 + (0.0000000046844)(\text{TZA})^3 - 1611.1$$

$$\text{ENTH(TZA,13)} = (5.8643)(\text{TZA}) + (0.002007)(\text{TZA}^2) - (0.00000051072)(\text{TZA})^3 - 269.49$$

$$\text{ENTH(TZA,14)} = (5.8945)(\text{TZA}) + 0.00098873(\text{TZA})^2 - (0.00000013018)(\text{TZA})^3 - 10.43$$

where enthalpy is in BTU/mole and TZA is in °F. The at least one signal 86 is established by the means 88 in response to a set point signal 90 which is representative of a desired flame temperature in the furnace 2. The signal 90 is received by the means 88.

A signal 92 representative of XHA is established by a suitable means 94 for establishing a signal representative of the moisture content of air entering conduit 6. The signal 92 is received by the computer 56. Preferably, the means 94 comprises a computer or subassembly capable of solving the relationship:

$$\text{XHA} = [10^{**}(5.319480 + (-0.00058601588 * \text{TDEW})$$

-continued $$+(-2119.6319/(301.00159+TDEW))]/$$

$$[PATM-(10^{**}(5.319480+(-0.00058601588$$

$$*TDEW)+(-2119.6319/(301.00159+TDEW))]$$

where XHA is representative of the ratio moles water/moles dry air, TDEW is the dew point temperature in °F. of air entering the conduit 6 and PATM is the atmospheric pressure in inches of mercury at which the dew point was obtained. The signal 92 is established by the means 94 in response to a signal 96 and preferably a signal 100. The means 94 receives the signal 96, which is established by a suitable means 98 for establishing a signal representative of the dew point of process air entering the conduit 6, such as a dew point transducer. The signal 96 is representative of TDEW. The signal 100 is representative of the pressure of air entering the conduit 6 and established by a suitable means 102 for establishing a signal representative of the pressure of process air entering the conduit 6, such as a pressure transducer. The signal 100 is received by the means 94. The signal 100 is representative of PATM.

A signal 104 representative of FAIR is established by a suitable means 106 for establishing a signal representative of the standardized flow rate of air through the conduit 6. The signal 104 is received by the computer 56. Devices suitable for performing the function of means 106 are well known by those having ordinary skill in the art. The signal 104 is established by the means 106 in response to a signal 108, a signal 112 and a signal 116. Preferably, the signal 104 is representative of FAIR in units of 1000 standard cubic feet per hour. The signals 108, 112 and 116 are received by the means 106. The means 106 receives the signal 108 which is representative of fluid flow rate through the conduit 6 from a means 110 associated with the conduit 6 for establishing a signal representative of fluid flow, such as a flow transducer. The signal 112, which is representative of the fluid pressure in the conduit 6 is established by a means 114 associated with the conduit 6 for establishing a signal representative of the fluid pressure in the conduit 6, such as a pressure transducer. The signal 116, which is representative of the temperature of fluid in the conduit 6 is established by a means 118 associated with the conduit 6 for establishing a signal representative of the temperature in the conduit 6, such as a temperature transducer.

In accordance with another aspect of the present invention, the rate of quench fluid flow in the conduit 14 is controlled in response to a signal which is derived at least in part from the moisture content of air entering the conduit 6. The apparatus 2 is thus provided with a means 119 associated with the quench fluid conduit 14 for controlling the quench fluid flow rate through the conduit 14 in response to a modified quench fluid flow rate set point signal 126 derived at least in part from the moisture content of air entering the conduit 6 and a signal 128 representative of the rate of fluid flow through the quench fluid conduit 14. Preferably, the means 119 comprises a flow controller 124 which receives the signals 126 and 128 and establishes a signal 122 in response to the signals 126 and 128 which is received by a valve 120, such as a motor valve, associated with the conduit 14. The valve 120 is manipulated in response to the signal 122 to control the rate of fluid flow through the conduit 14. The signal 122 can be electrical, hydraulic, mechanical, or pneumatic in nature, for example, and is derived at least in part from the moisture content of the air entering the conduit 6. The signal 128 is established by a means 130 associated with the conduit 14 for establishing a signal representative of the flow rate of quench fluid in the conduit 14, such as a flow transducer. The signal 126, which is representative of the desired flow rate of quench fluid, is derived at least in part from the moisture content of the air entering the conduit 6 by a means 131 for establishing a modified quench fluid flow rate set point signal derived at least in part from the moisture content of air entering the air conduit. Preferably, the means 131 comprises a means 133 for establishing a quench fluid flow rate modifying signal 134($\Delta$FH20) derived at least in part from the moisture content of air entering the conduit 6, and a means 135 for establishing a quench fluid flow rate set point signal 178 derived at least in part from the temperature of the quenched effluent flowing through the conduit 10. The modified signal 126 is established in response to a relationship between the set point signal 178 and the modifying signal 134.

Preferably, the quench fluid flow rate modifying signal is established in response to a relationship between:

(a) the temperature of the quench fluid flowing through the conduit 14 (TH20);

(b) the air flow rate through the conduit 6 (FAIR);

(c) the moisture content of air entering the conduit 6 (XHA);

(d) the moisture content of air entering the conduit 6 at a previous time (XHAR);

(e) the enthalpy of water vapor near the intake of the conduit 6 (ENTH(TAMB,9)); and (f) the enthalpy of water vapor in the quenched effluent stream in conduit 10 (ENTH(TMSO,9) and (ENTH2(TMSO,9)).

Preferably, the relationship between the above parameters is established by a computer 132 which establishes the signal 134. For example, a suitable relationship for establishing the signal 134 in response to the above parameters can be expressed as:

$$\Delta FH20 = [FAIR*(1000/379)*(XHA\text{-}XHAR)$$

$$*(ENTH(TSMO,9)-ENTH(TAMB,9))*18.015]$$

$$/(ENTH2(TSMO,9)+19658-18.015*TH20)$$

where $\Delta$FH20 is representative of the signal 134.

A signal 138 representative of TH20 is established by a means 140 associated with the conduit 14 for establishing a signal representative of the temperature of the fluid flowing through the conduit 14, such as a temperature transducer. The signal 138 is received by the computer 132.

A signal 142 representative of FAIR is established by the means 106 or its equivalent for establishing a signal representative of fluid flow through the conduit 6. The signal 142 is received by the computer 132.

A signal 144 representative of XHA is established by the means 94 or its equivalent for establishing a signal representative of the water content of the air entering the conduit 6. The signal 144 is received by the computer 132.

A signal 146 representative of XHAR is established by a means 148 for establishing a signal representative of the water content of the air entering the conduit 6 at a previous point in time. As shown, the means 148 is a delay switch as well known by those having ordinary skill in the art which receives a signal 150 representative of XHA from the means 94 or its equivalent for establishing a signal representative of the mole ratio water vapor/dry air of the air entering the conduit 6, and, after a suitable delay period, which can range from milliseconds to minutes, for example, six seconds, transmits the previously received XHA signal as XHAR to the computer 132.

A signal 152 representative of ENTH(TAMB,9) is established by a means 154 for establishing a signal representative of the enthalpy of water vapor in air entering the conduit 6. Preferably, means 154 is a computer or subassembly capable of solving the relationship.

$$ENTH(TAMB,9) = (7.93163)(TAMB) + (0.000711015)(TAMB)^2 - 414.95$$

where TAMB is ambient temperature in °F. and ENTH(TAMB,9) is measured in BTU/mole. The relationship is solved by the means 154 in response to a signal 156 representative of TAMB which is established by a means 158 for establishing a signal representative of the ambient temperature adjacent the intake to the conduit 6 such as a temperature transducer. The signal 156 is received by the means 154.

Signals 160 and 162 representative of ENTH(TSMO,9) and ENTH2(TSMO,9) are established by means 164 and 166, respectively, for establishing a signal representative of the desired enthalpy of water vapor in the quenched effluent flowing through the conduit 10 and entering into indirect heat exchange relationship with the air in the air conduit 6. The signals 160 and 162 are received by the computer 132. Preferably, the means 164 is a computer or subassembly capable of solving the relationship $$ENTH(TSMO,9) = (7.93163)(TSMO) + (0.000711015)(TSMO)^2 - 414.95$$

and the means 166 is a computer or subassembly capable of solving the relationship $$ENTH2(TSMO,9) = (7.93163)(TSMO) + (0.000711015)(TSMO)^2$$

where ENTH is in BTU/mole and TSMO is an °F.

The signals 160 and 162 are established by the means 164 and 166 in response to at least one set point signal 168 representative of TSMO. TMSO is representative of a temperature which is determined by the metallurgical limit of equipment downstream of the conduit 10. Usually, TSMO is representative of a temperature of 1500° F. or less.

A signal 172 representative of the temperature of the quenched effluent in the conduit 10 is established by a means 170 associated with the conduit 10, such as a temperature transducer. The signal 172 is received by a temperature controller 174. The temperature controller establishes a signal 178 in response to the signal 172 and a set point signal 176 which is representative of the desired temperature of the effluent in the conduit 10 to provide the signal 178 which is representative of a desired flow rate of quench fluid through the conduit 14 derived at least in part from the temperature of the quenched effluent flowing through the conduit. The signal 176 is representative of a temperature of less than the temperature at which equipment damage would occur, for example, a temperature of 1400° F.

The signals 134 and 178 are received by a means 180 for modifying the set point signal 178 with the modifying signal 134 according to a predetermined relationship. The means 180 can be a summing junction, well known to those having ordinary skill in the art. The means 180 establishes the signal 126 which is received as the modified set point signal by the flow controller 124.

While the invention has been described in detail for purposes of explanation and illustration, it is not intended to be limited thereby. Rather, reasonable modifications and additions which would be apparent to one with ordinary skill in the art are included within the scope of this invention.

What is claimed is:

1. In a process for the production of carbon black comprising
    combusting a stream of fuel with a stream of air to form a stream of combustion gases;
    reacting a carbonaceous feedstock with said combustion gases to produce carbon black;
    introducing a stream of quench fluid into the stream of combustion gases to form a quenched effluent stream; and
    passing the quenched effluent stream into an indirect heat exchange relationship with the stream of air and thereafter recovering carbon black; the improvement comprising:
    controlling the rate of introduction of the quench fluid stream into the stream of combustion gases in response to a first signal which is derived at least in part from the moisture content of the air entering the stream of air.

2. A process as in claim 1 further comprising:
    (a) establishing a second signal representative of the rate of introduction of the quench fluid stream into the stream of combustion gases;
    (b) establishing a third signal representative of a desired rate of quench fluid flow derived at least in part from the moisture content of the air stream;
    (c) comparing the second signal to the third signal; and
    (d) establishing the first signal in response to the comparison between the second signal and third signal.

3. A process as in claim 2 further comprising:
    (a) establishing a fourth signal in response to a comparison between a signal representative of the temperature of the quenched effluent stream and a signal representative of a desired temperature of the quenched effluent stream;
    (b) establishing a fifth signal derived at least in part from the moisture content of the air stream; and
    (c) establishing the third signal in response to a predetermined relationship between the fourth signal and the fifth signal.

4. A process as in claim 3 wherein the predetermined relationship between the fourth signal and the fifth signal is a summation.

5. A process as in claim 4 wherein the fifth signal is representative of a desired change in the rate at which quench fluid is introduced into the stream of combustion gases.

6. A process as in claim 5 wherein the fifth signal is established in response to a predetermined relationship between
    (a) a sixth signal representative of the temperature of the air stream;

(b) a seventh signal representative of the pressure of the air stream;

(c) an eighth signal representative of the flow rate of the air stream;

(d) a ninth signal representative of the dew point of air entering the air stream;

(e) a tenth signal representative of the pressure of air entering the air stream;

(f) an eleventh signal representative of a desired temperature of the quenched effluent stream;

(g) a twelfth signal representative of the temperature of air entering the air stream; and (h) a thirteenth signal representative of the temperature of the quench fluid stream.

7. A process as in claim 6 wherein (a) a fourteenth signal representative of the standardized flow rate of air in the air stream is established in response to the sixth, seventh and eighth signals;

(b) a fifteenth signal representative of the moisture content of the air stream is established in response to the ninth and tenth signals;

(c) a sixteenth signal representative of the moisture content of the air stream at a previous time is established in response to the fifteenth signal;

(d) at least one seventeenth signal representative of the enthalpy of water vapor at the desired temperature of the quenched effluent stream is established in response to the eleventh signal; and (e) an eighteenth signal representative of the enthalpy of water vapor at the temperature of the air entering the air stream is established in response to the twelfth signal.

8. A process as in claim 7 comprising relating the thirteenth signal, the fourteenth signal, the fifteenth signal, the sixteenth signal, the seventeenth signal and the eighteenth signal according to the relationship $$(FAIR * 1000/379) * (XHA\text{-}XHAR) *$$

$$((ENTH\,(TSMO,\,9) - ENTH\,(TAMB,\,9)) * 18.015)$$

$$/(ENTH2\,(TSMO,\,9) + 19658 - 18.015 * TH20)$$

wherein
FAIR is the fourteenth signal,
XHA is the fifteenth signal,
XHAR is the sixteenth signal,
ENTH (TSMO, 9) is a first seventeenth signal,
ENTH (TAMB, 9) is the eighteenth signal,
ENTH2 (TSMO, 9) is a second seventeenth signal, and
TH20 is the thirteenth signal
and establishing the fifth signal in response thereto.

* * * * *